United States Patent [19]

Bseisu et al.

[11] Patent Number: 5,038,614

[45] Date of Patent: Aug. 13, 1991

[54] ACOUSTIC VIBRATION DETECTION OF FLUID LEAKAGE FROM CONDUITS

[75] Inventors: Amjad A. Bseisu; John E. E. Kingman, both of Dallas; H. Mitchell Cornette, Plano, all of Tex.

[73] Assignee: Atlantic Richfield Company, Los Angeles, Calif.

[21] Appl. No.: 391,919

[22] Filed: Aug. 10, 1989

[51] Int. Cl.[5] ............................................. G01N 29/04
[52] U.S. Cl. ..................................... 73/592; 376/252; 73/597; 73/598; 73/40.5 A
[58] Field of Search ..................... 73/40.5 A, 592, 597, 73/598; 376/252

[56] References Cited

U.S. PATENT DOCUMENTS

| | | | |
|---|---|---|---|
| 2,677,270 | 5/1954 | Sanderson | 73/592 |
| 3,413,653 | 11/1968 | Wood | 73/40.5 A |
| 3,889,522 | 6/1975 | Mayo | 73/40.5 P |
| 4,289,019 | 9/1981 | Claytor | 73/40.5 A |
| 4,541,278 | 9/1985 | Marsh et al. | 73/592 |
| 4,543,817 | 10/1985 | Sugiyama | 73/40.5 A |

FOREIGN PATENT DOCUMENTS

| | | | |
|---|---|---|---|
| 0101746 | 5/1988 | Japan | 73/40.5 A |
| 1312426 | 5/1987 | U.S.S.R. | 73/592 |
| 1128704 | 10/1968 | United Kingdom | 73/40.5 A |

Primary Examiner—Hezron E. Williams
Assistant Examiner—Rose M. Finley
Attorney, Agent, or Firm—Michael E. Martin

[57] ABSTRACT

Fluid leakage from a crack or other leakage point and other vibration-generating events in pipes and conduits may be located and analyzed by sensing axial and torsional vibrations and pressure fluctuations created by such events by placing accelerometers and/or strain gauges and pressure sensors on the conduit at selected points. The location of the event may be determined by comparing the travel time of selected pairs of signals such as axial propagated signals as compared with torsional propagated signals as a result in the difference of the acoustic wave speed of axial versus torsional waves. Cross correlation and deconvolution processes are carried out on the measured signals to determine differential signal arrival times at the sensors and to eliminate pipe response signals. An apparatus having axial and torsional vibration sensing accelerometers thereon includes mechanism for clamping the apparatus to the inside wall of the tubing or pipe and sensing the vibratory output signals of the accelerometers to determine the nature of and location of the vibration inducing event.

18 Claims, 6 Drawing Sheets

ACOUSTIC VIBRATION DETECTION OF FLUID LEAKAGE FROM CONDUITS

BACKGROUND OF THE INVENTION

1. Field of the Invention

This invention pertains to a method and system for detecting leakage of fluid into or out of conduits and vessels and other events associated with such conduits by measurement of acoustic vibrations.

2. Background

The detection and analysis of acoustic vibrations in certain structures can be advantageously utilized to control or determine particulars of the behavior of the structures in environments wherein visual inspection is impossible or inconvenient. U.S. Pat. No. 4,715,451 issued to Amjad A. Bseisu et al and assigned to the assignee of the present invention describes a method and system for analyzing the behavior of an elongated drill stem by measuring acoustic vibrations and strain on the drill stem during operation.

It has been determined that other occurrences can induce detectable acoustic vibrations in elongated tubular members such as pipelines and in conduits associated with drilling, completing and producing wells. In this regard, since many pipelines and conduits for conducting fluid flow to and from wellbores are generally inaccessible for visual inspection, the detection of fluid leakage or certain operating functions associated with such conduits by measuring acoustic vibrations and strains on the conduits would seem to be beneficial. To this end the present invention has been developed with a view to providing a method and system for determining the characteristics and locations of leakage flow and certain events occurring in pipelines and similar conduits, particularly those associated with wells.

SUMMARY OF THE INVENTION

The present invention provides a method for determining the location of fluid leaks in conduits such as pipelines and wellbore conduits, for example. In accordance with an important aspect of the present invention, there is provided a method and system for measuring acoustic vibrations induced in a fluid conduit resulting from leakage flow of fluid through a crack or joint in the conduit. In accordance with one embodiment of the present invention, axial and/or torsional vibrations and strains on a conduit and/or fluid pressure fluctuations in the conduit are measured at spaced apart points and the frequency patterns of such vibrations are analyzed and compared to determine the location of fluid leakage or the occurrence some other event associated with the operation of certain mechanisms, such as valves, interposed in or connected to the conduit. The method and system of the invention may be advantageously used in determining the existence and location of leaks in buried or otherwise inaccessible pipelines and similar conduits, for example.

In accordance with another aspect of the present invention, there is provided a method and apparatus for determining the location of fluid leaks in pipes and wellbore conduits by measuring selected combinations of axial and torsional vibrations and fluid pressure fluctuations at a single point in the conduit. The method and system may also be advantageously used to determine if certain events are occurring or devices are functioning at certain locations in a conduit.

In one embodiment of the present invention, there is provided a sensing apparatus which is insertable in a pipe section and is adapted to be urged into engagement with the inner wall of the pipe section. Alternatively, the apparatus may be inserted in and lowered through a wellbore conduit over a relatively short distance from the surface or the normal point of entry of devices into the wellbore conduit and then urged into engagement with the conduit wall. The apparatus includes sensors for detecting axial and torsional vibrations of the conduit and fluid pressure fluctuations in the conduit induced by (1) fluid flow through certain leakage paths in the conduit or (2) by certain devices interposed in the conduit. For example, the operation of certain devices such as gas lift valves may be detected with respect to the location of these valves in the conduit system. The sensing apparatus is adapted to measure axial and torsional vibrations and pressure fluctuations. The characteristics of these vibrations may be compared to determine the location of a leak in the conduit or the operation of the particular mechanism in the conduit.

The above-described advantages and features of the present invention together with other superior aspects thereof will be further appreciated by those skilled in the art upon reading the detailed description which follows in conjunction with the drawing.

DESCRIPTION OF PREFERRED EMBODIMENTS

In the description which follows, certain elements which are commercially available may be described in general terms only and the drawing figures may illustrate certain components in schematic form in the interest of clarity and conciseness.

Figure 1:
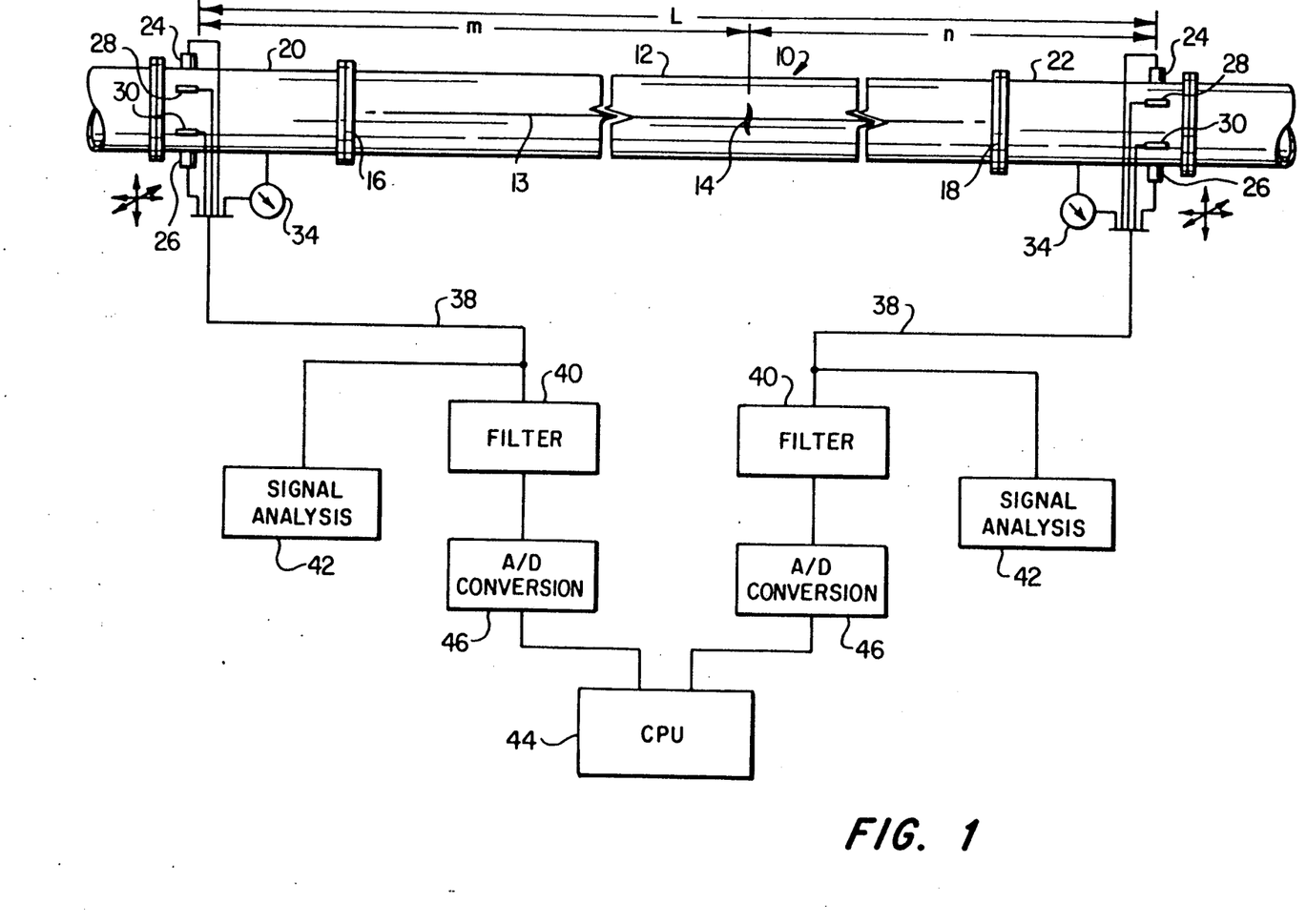
FIG. 1 is a schematic diagram of a section of fluid transmission pipeline which has been modified to include a system for detecting the location of a leak in the pipeline.

Referring to FIG. 1 there is illustrated a schematic diagram of a fluid transmission pipeline generally designated by the numeral 10 having a section 12 in which a transverse or lateral crack 14 has occurred and through which leakage flow of fluid from the interior of the pipeline may occur. This leakage flow in the form of a gas or liquid may, depending on the internal pressure generated within the pipeline 10, escape through the crack 14 with sufficient energy dissipation to induce certain vibrations which are propagated along the pipeline in opposite directions. These vibrations may be detected by devices including sensitive accelerometers and strain gauges generally of the type described in U.S. Pat. No. 4,715,451.

In order to detect the possibility of fluid leakage flow from a joint in the pipeline, such as the flanged joints 16 and 18, for example, or from the crack 14, it is contemplated to provide at least one section of pipeline, generally designated by the numeral 20 and preferably a second section 22 which are suitably instrumented with certain types of accelerometers and/or strain gauges and pres-sure transducers to detect the vibrations caused by leakage flow at the crack 14 or at the joints 16 and 18. The pipe section 20 may be a special section insertable in the pipeline 12 or the aforementioned accelerometers and strain gauges may be attached directly to the sections 20 and 22 comprising permanent portions of the pipeline 12.

As illustrated, the section 20 includes diametrically opposed accelerometers 24 and 26 mounted thereon together with certain strain gauges 28 and 30, also mounted on the surface of the pipe section 20. In like manner, the pipe section 22 is also adapted to include diametrically opposed accelerometers 24 and 26 mounted thereon and, in a similar manner separate, strain gauges 28 and 30. The accelerometers 24 and 26 may each be of the so-called tri-axial type. The accelerometers 24 and 26 are capable of measuring displacements in a direction parallel to the longitudinal central axis 13 of the pipeline 12, in a direction normal to the axis 13 and along a line passing through the axis and in a direction normal to the axis 13 and along a tangent to the circumference of the pipe sections 20 and 22. In this way the accelerometers 24 and 26 are adapted to produce signals which indicate axial vibrations along the pipe 12, lateral vibrations and torsional vibrations about the axis 13. The strain gauges 28 are adapted to measure compressional and torsional vibrations along the axis 13 and the strain gauges 30 may be of the semiconductor resistor type for measuring surface waves that are generated and travel along the outer surface of the pipe 12 including the sections 20 and 22. The pipe sections 20 and 22 may be connected to the pipe section 12 by way of conventional flanged joints or by other conventional means of joining one pipe section to another.

The measurement processes of the present invention could, of course, typically include monitoring the pressure in the pipeline 12 by way of pressure sensors 34 to detect the onset and location of leakage. The signals generated by the sensing devices comprising the accelerometers 24 and 26, the strain gauges 28 and 30 and the pressure sensors 34 are transmitted by suitable conductor means 38, or by telemetry techniques, through suitable signal filter devices 40 for eliminating spurious and unwanted output signals. Signals may be instantaneously monitored and developed through suitable signal analyzers 42 and filtered signals may be input to a central processing unit 44 by way of suitable analog to digital conversion circuits 46.

It has been determined that the energy of a flow-stream of a liquid, gas, or a multiphase mixture of both, under significant pressure emanating from a crack such as the crack 14, or a leaky joint in a pipeline or vessel, is converted to vibratory motion of the vessel, or pipeline, and certain frequency bands and amplitude levels of these signals may indicate the orientation of the crack or leakage path as well as the location thereof. In particular, for a section of pipeline instrumented generally in accordance with the arrangement of FIG. 1, signals of a particular frequency band sensed by the respective sets of accelerometers and strain gauges on the sections 20 and 22 may be compared to determine the location of the leak or other anomaly which is occurring and which has generated the vibratory motion of the pipeline section such as the section 12. By comparing the relative arrival times of signals within a certain frequency bandwidth at the respective sensors mounted on the pipe sections 20 and 22 and with the knowledge of the speed of acoustic compressional or torsional waves in the material of which the pipe section 12 and the sections 20 and 22 are fabricated, or the acoustic velocity of the fluid in the pipeline in the case of measuring fluid pressure fluctuations, the location of the crack 14 may be determined.

Figure 2:
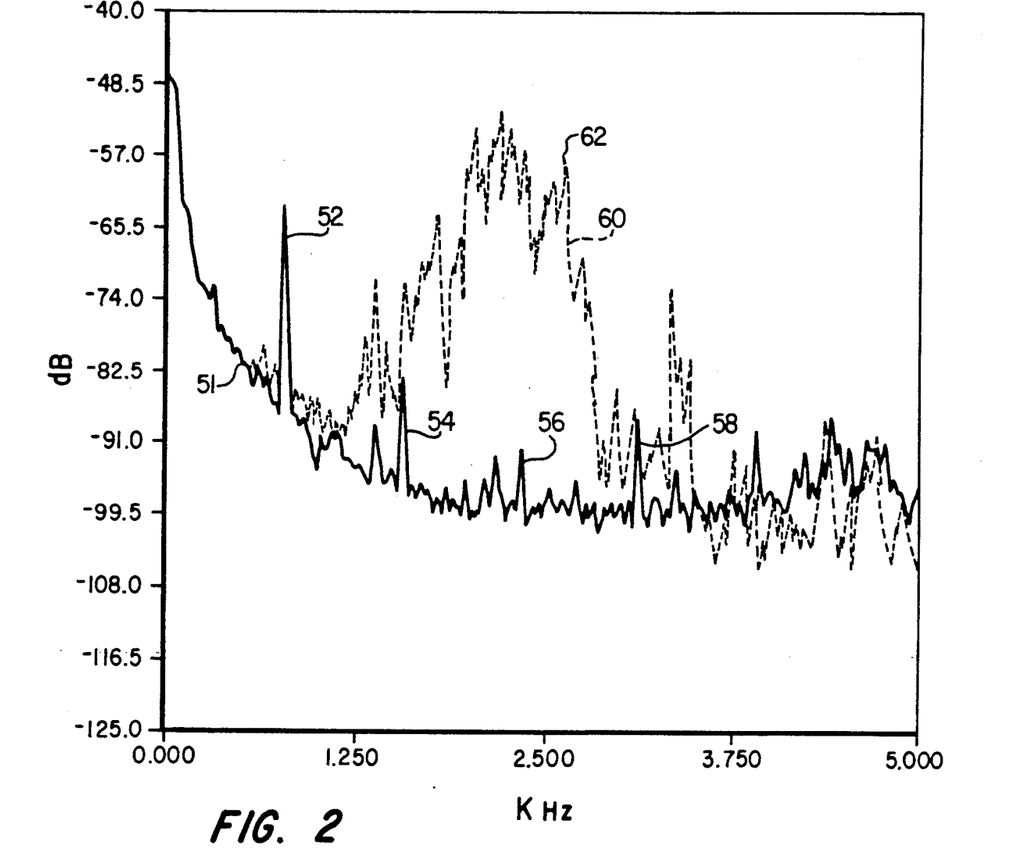
FIG. 2 is a diagram showing the characteristic of axial vibrations over a selected frequency range for a fluid transmission pipeline through which fluid is being pumped by a reciprocating pump without any leakage in the pipeline and for leakage through a small lateral crack in the pipeline.

For example, referring to FIG. 2, there is illustrated a diagram showing a plot of a certain frequency band of oscillatory signals generated by one of the accelerometers 24 or 26 in the direction of the axis 13. In FIG. 2, the frequency range of the signal which is sampled by the system illustrated in FIG. 1 is between 0 Hz and 5000 Hz. The signal represented by line 51 includes sharp peaks 52, 54, 56 and 58, for example, which are axial strains or vibrations induced by the pressure pulsations of a reciprocating plunger pump which is pumping fluid through the pipeline 10. Selected harmonics of the pumping frequencies are indicated by the peaks 54, 56 and 58 as well as certain other intermediate and higher frequency peaks which indicate possible harmonics of the fundamental pump delivery pulse frequency. The signal represented by the line 51 over the frequency spectrum or bandwidth illustrated in FIG. 2 indicates a fairly constant amplitude signal over a substantial portion of the bandwidth, particularly between approximately 1.0 kHz and 5.0 kHz except, of course, for the peak amplitude signals indicating multiples of the pump pulsation frequency. However, the signal characteristic indicated by the line 60 results from measuring the output signal of an accelerometer 24 or 26 for a leak from a crack 14 of approximately one-eighth inch length and width for a condition of water escaping from the crack at a pressure of approximately 200 psig within the pipeline 10 and comprising a steel pipe of about 7.0 inches diameter. The signal amplitude indicated by the line 60 indicates significant vibrational energy being transmitted through the pipe 10 to the transducers 24 and 26 in a frequency band from about approximately 1.25 kHz to approximately 3.5 kHz.

By selecting a particular signal of peak amplitude at a selected frequency band such as the peak 62 at approximately 1.0 kHz to 2.6 kHz, the difference in the arrival times of the vibratory pulse which generates this signal at the respective sets of pressure transducers or accelerometers and strain gauges on the respective measurement sections 20 and 22 may be determined and the distance of the leak or crack 14 from the measurement sections 20 and 22 can be readily determined for a pipe or conduit wherein the material and, thus, the acoustic velocity is known and wherein the total distance L (FIG. 1) between the sensors on the measurement sections 20 and 22 is known. The distance m from the sensors of measurement section 20 to the crack 14 may be determined from the equation:

$$m = \frac{\Delta t \cdot V_a + L}{2}$$

where $\Delta t$ is the time difference between the arrival times of the signals indicating the axial vibrations caused by the leak at crack 14 at the sensors of the respective measurement sections 20 and 22 and $V_a$ is the acoustic velocity of an axial wave propagating along the pipe section 12.

Torsional vibrations or pressure fluctuations may also be compared at the measurement sections 20 and 22 as regards their relative arrival times and the torsional wave speed of the pipe section 12 or acoustic velocity of the fluid in the pipe used in the above equation as the case may be. Of course, the distance n is equal to L−m. The location of the crack 14 may also be measured at a single point on the pipe section 12 at either of the measurement sections 20 or 22, for example, by determining the arrival time of a torsionally propagated signal at the sensors of one of the measurement sections from the crack 14 as compared with the arrival time of an axially propagated signal at the same measurement section and caused by the same event. The distance m (or n) may be determined from the equation:

$$m = \frac{V_r \cdot V_a \cdot \Delta t}{\Delta V}$$

wherein: $V_r$=the velocity of the torsional stress wave,
$V_a$=the velocity of the axial stress wave,
$\Delta V = V_a - V_r$, and
$\Delta t$=the difference in arrival time of the axial and torsionally propagated wave signal at the sensors of measurement section 20.

Axial or torsional vibrations may also be compared with pressure fluctuations sensed by the sensors 34 and in such case the value of the acoustic velocity of the fluid $(V_f)$ may be substituted for the omitted wave velocity in the above equation.

Moreover, for a signal which is transmitted as an axial compressional or torsional vibration to one or both of the measurement sections 20 and 22, a time history record of the signal may be determined to ascertain signal correlation or, in other words, a determination as to whether or not the signals are resulting from the same event.

Figure 3:
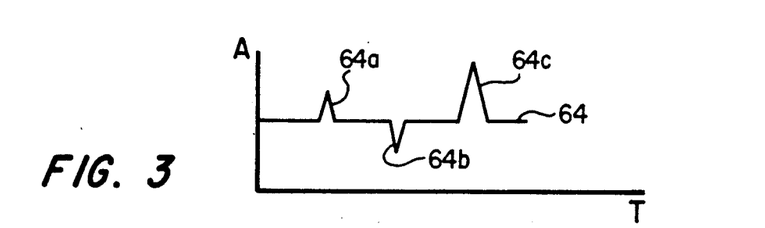
FIGS. 3 and 4 are diagrams illustrating one mode of determining signal correlation.
Figure 4:
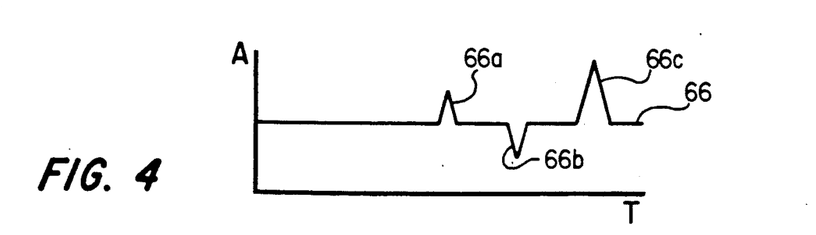

For example, referring to FIGS. 3 and 4 analysis of a particular signal, measured at section 20 such as the signal indicated at the peak 62, when plotted as a function of time, may have a characteristic as indicated by the line 64. If a signal measured at the other measurement section 22 or, by measuring torsional vibrations at the sections 20 or 22, has a similar characteristic when plotted as a function of time, such as indicated by the line 66 in FIG. 4, that is peaks 66a, 66b and 66c which correspond to peaks 64a, 64b and 64c, the coherency of these signals is confirmed and they may be compared to determine the location of the leak or some other signal producing event.

If the signals indicated in FIGS. 3 and 4 are based on sensing axial vibrations, for example, at the measurement sections 22 and 20, respectively, the time difference ($\Delta t$) of the arrival times of the signal at the respective measurement sections may be determined by a cross-correlation technique. Such a technique typically involves, for a relatively complex signal, selecting values of the signal at relatively small increments of time for each of the signals 64 and 66 and at each time increment ($t_1, t_2, t_3...$) the respective signal amplitudes or a related value, for each of the signals 64 and 66 are multiplied and summed to develop a cross-correlation signal. The incremental values are shifted in time and summed until a peak summation value is obtained as a function of time shift and this time shift is determined to be the time difference between the arrival of the same signal at the sensors of the measurement section 20 versus the sensors of the measurement section 22.

In the instance where only one measurement section 20 or 22 is being used and torsional versus axial, axial versus pressure or torsional versus pressure vibrations are being correlated, the same technique may also be employed. In such an instance, for example, the characteristic of FIG. 3 might indicate an axial propagated signal and the characteristic or curve 66 of FIG. 4 might indicate a torsionally propagated signal. Certain references which discuss basic analysis for the cross-correlation technique include the treatise entitled: "Random Data Analysis and Measurement Procedures", 2nd Edition, J. S. Bendat and A. G. Piersol, John Wylie & Sons, New York, 1986. Cross-correlation techniques are also described in publications entitled "Technical Review", Nos. 1 and 2, 1984 by Bruel and Kjaer Instruments, Inc., Marlboro, Mass.

For relatively narrow-band signals, the impulse response function may yield a better or more accurate definition of the time delay between receipt of the signals at the respective measurement sections or the receipt of axial and torsional signals at just one of either of the measurement sections. Unit impulse response measurements are discussed in the publication entitled "Engineering Applications of Correlation and Spectral Analysis" by J. S. Bendat and A. G. Piersol, John Wylie & Sons, New York, 1980.

The assumption that acoustic wave forms created at the crack 14 due to fluid leakage flow or similar energy-generating events are not significantly altered as they travel along the pipe section 12 or a tubing string or the like relies on the premise that there is little effect on the signal due to response of the pipe or tubing sections themselves. This assumption may be relatively accurate for vibrations in the range of 0 Hz to 100 Hz. However, above 100 Hz, signal reflections of stress waves are created at the flanges 16 and 18, for example, to shape or alter the signal wave forms. The result of this phenomenon is to prohibit the transmission of signals in certain frequency bands and to significantly change signal patterns. However, a deconvolution process may be used to remove the effect of the altered wave form due to the presence of the flanges 16 and 18 or other structural features which tend to distort the wave forms as they travel along the pipe or tubing. The deconvolution process does require predicting or measuring the response of the pipeline 10 to the signals caused by leakage at the crack 14 and then subtracting the effects of the pipeline response from the measured signals at the sensors of the measurement sections 20 and 22.

Measurement of the difference in arrival time ($\Delta t$) of two signals indicating an event such as leakage flow from a pipe section 12, for example, and having time records such as shown in FIGS. 3 and 4 may be determined by:

(1) Subjecting a plurality of multiple point consecutive zero padded time records for each signal, i.e. axial and torsional, to fast Fourier transform analysis of time domain data to produce what are known in the art of signal analysis as the auto spectra values $G_{aa}$ (axial) and $G_{rr}$ (torsional). The auto spectra values are the magnitude of the Fourier transforms squared or the product of the Fourier transform and its complex conjugate, and are running average values, respectively.

(2) Calculating the cross spectra values, $G_{ar}$, which comprise the product of the complex conjugates of the Fourier transforms of the respective series of axial and torsional time records.

(3) Measuring (or predicting) the frequency response of the pipe or tubing section through which the signals are transmitted which provide the auto spectra values of paragraphs (1) and (2) for both axial and torsional modes. These frequency response values, $R_a$ and $R_r$, if determined from actual pipe response measurements, may be obtained by:

(a) impacting the pipe at a predetermined point with a known signal, h(t), whose amplitude-time characteristic is measured, using an instrumented hammer, for example;

(b) measuring the signal received, a(t), axial, for example, as a function of time (and which may be either axial or torsional, as per the type of impact signal input to the pipe);

(c) performing fast Fourier transform analysis of the time domain data to obtain the auto spectra, $G_{hh}$, and the cross spectra, $G_{ha}$, all as running averages;

(d) determining the frequency response of the pipe from the relationship;

$$R_a = \frac{G_{ha}}{G_{hh}}$$

If torsional frequency response is being determined the relationship is:

$$R_r = \frac{G_{hr}}{G_{hh}}$$

using the steps of paragraph (1), where $G_{hh}$ is the auto spectra of the transformed hammer signal and $G_{hr}$ is the cross spectra of the torsional and hammer (impact) signals, (4) deconvolving the pipe or tubing response signal by performing the calculations:

$$\frac{G_{ar}}{G_{aa}} \cdot \frac{R_a}{R_r}$$

or $$\frac{G_{rr}}{G_{ar}} \cdot \frac{R_a}{R_r}$$

(5) performing inverse Fourier transform analysis on the products of the above-noted relationships of paragraph (4); and (6) plotting the resultant values, which is the impulse response, as a function of time and determining where a peak value of such resultant values occurs on a time scale. This peak value, as a function of time from t=0, is the time difference between an axial and torsional signal arriving at the same measurement section. Alternatively, of course, two axial signals or two torsional signals or two pressure fluctuation signals sensed at spaced apart measurement sections, such as the measurement sections 20 and 22, may be compared. Still further, axial or torsional signals may be compared with a pressure fluctuation signal arriving at the same measurement section.

Since a correlation between signals of an axial propagation mode through a conduit, such as a pipe or tubing string, and a torsional propagation mode through such conduit may be made in accordance with the method of the present invention, (or correlation between an axial or torsional propagated signal and a pressure wave propagated signal), the placement of measurement devices such as the transducers 24 and 26, the strain gauges 28 and 30 and the pressure sensors 34 at spaced apart points on each side of the section to be monitored is not required. In this regard the present invention also contemplates an apparatus as illustrated in FIGS. 5A through 5G which may be inserted in a tubing or pipe string at a predetermined location and suitably brought into contact with the sidewall of the pipe or tubing for measuring the transmission of axial and torsional vibrations through the pipe for determining the location of a leak or the functioning of certain devices which are capable of generating vibrations in the pipe. In particular, an apparatus such as illustrated in FIGS. 5A through 5G may be inserted in tubing or conductor pipe strings associated with oil and gas wells to determine the location of leaks or the functioning of certain devices in the tubing string such as gas lift valves and the like.

Figure 5A:
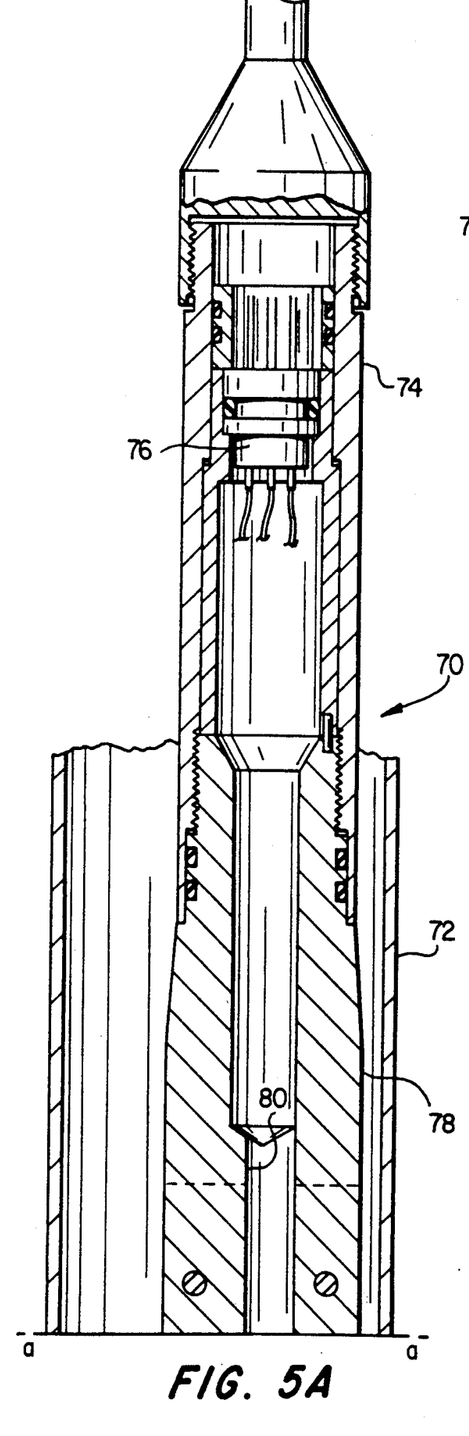
FIGS. 5A through 5G comprise a longitudinal central section of an apparatus insertable in a wellbore conduit for measuring the location of leakage flow from the conduit or the operation of certain mechanisms associated with the conduit.
Figure 5B:
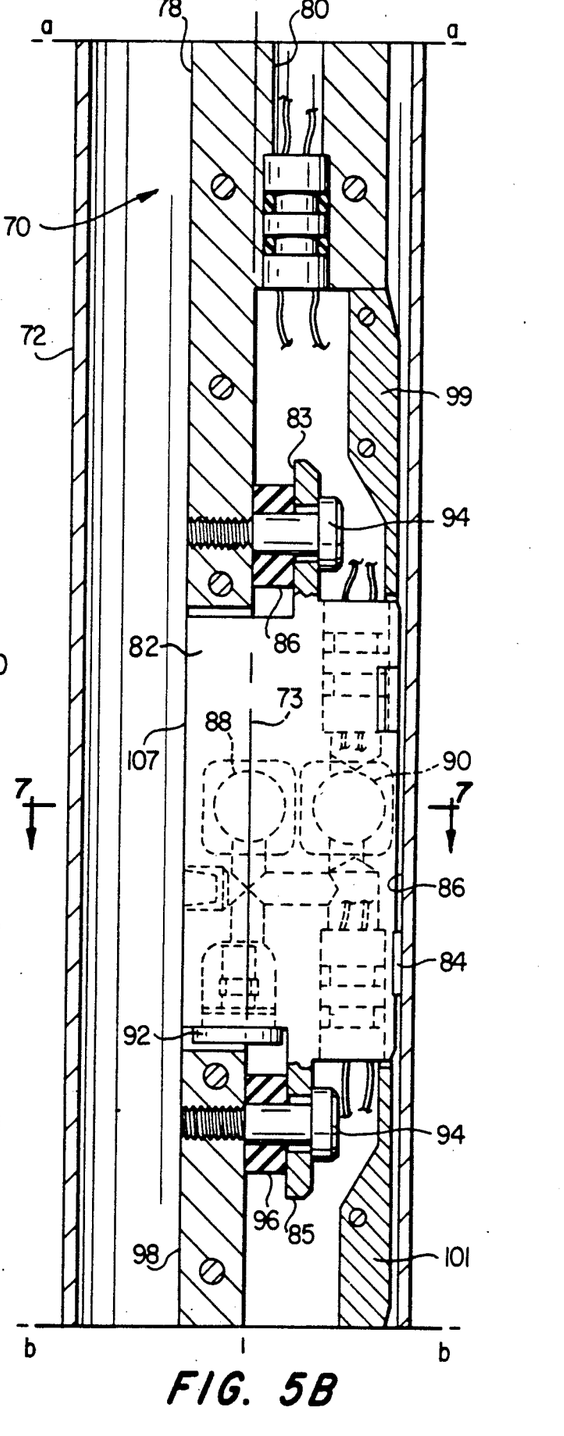

Referring to FIGS. 5A through 5G, the apparatus illustrated is generally designated by the numeral 70 and is shown inserted in a section of tubing string 72 which may be, for example, a production tubing string for an oil or gas well. The apparatus 70 may be inserted in the tubing string 72 utilizing conventional equipment for lowering the apparatus into a section of the tubing string just below a wellhead, not shown, for example. Conventional wireline equipment or coiled tubing injection equipment may be used for such an insertion and placement function. The apparatus 70 is provided with a head portion 74 which is adapted to be connected to a "wireline" type, multiconductor electrical cable, not shown and is provided with a suitable plug member 76 for interconnecting plural electrical conductors within the apparatus 70 with conductors of the wireline cable. The head member 74 is connected to an elongated body part 78 having a central passage 80 formed therein for extension of plural electrical conductors therethrough. As shown in FIG. 5B, a sensor support body member 82 forms part of the apparatus 70 and, as shown in FIG. 6, is provided with three spaced apart tubing engaging contact lugs or projections 84 to provide firm contact of the body member with the inner wall 86 of the tubing 72. The body member 82 is adapted to support a plurality of vibration sensors comprising piezoelectric accelerometers 88, 90 and 92. The accelerometers 88 and 90 are particularly adapted to measure movement in a direction normal to the longitudinal central axis 73 of the tubing string 72 and the accelerometer 92 is adapted to measure accelerations parallel to the axis 73. By providing two accelerometers for measuring so-called lateral vibrations, the output signals of these accelerometers may be compared to determine whether or not the body member 82 and the tubing 72 is vibrating in a torsional mode or in a lateral or transverse mode. The body member 82 is provided with suitable opposed flanges 83 and 85, as illustrated in FIG. 5B and FIG. 6. The body member 82 is also connected to a lower section of the apparatus 70 including a body member 98 by a second fastener 94 and bushing 96 engaged with flange 85. The afore-described support arrangement allows some flexing of the body part 82 with respect to the members 78 and 98 to assure that uniform contact by the lugs 84 is obtained with respect to the tubing wall 86. Removable cover plates 99 and 101 enclose part of the space between body members 78 and 98 which is occupied by the body member 82. Opposed side plates 107, one shown in FIG. 5B, extend along opposite sides of the apparatus 70 and are secured to the body members 78 and 98.

Figure 5C:
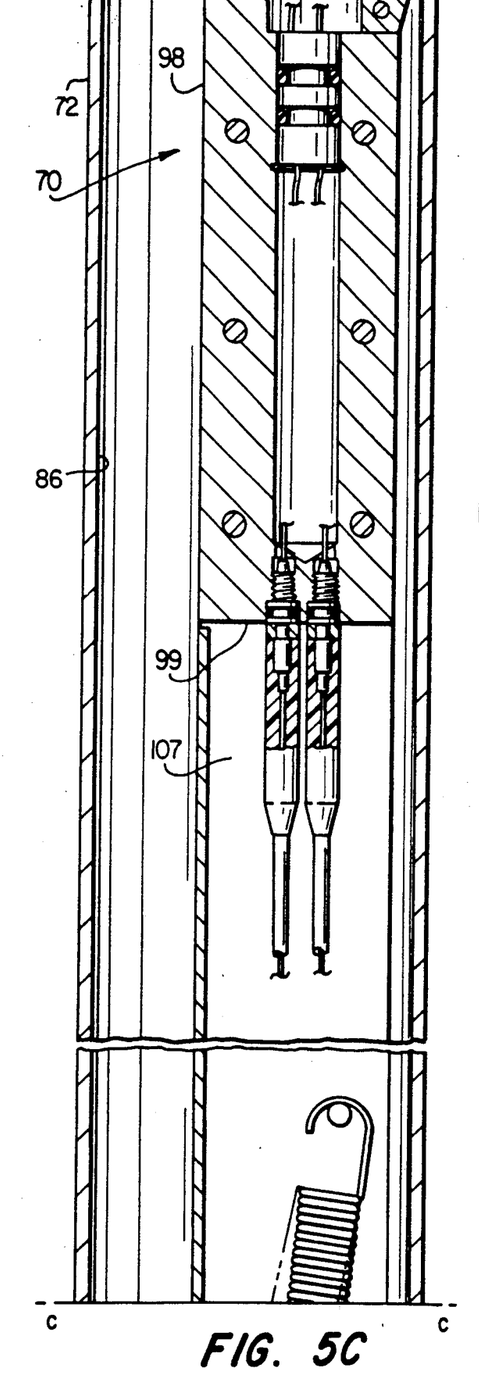
Figure 5D:
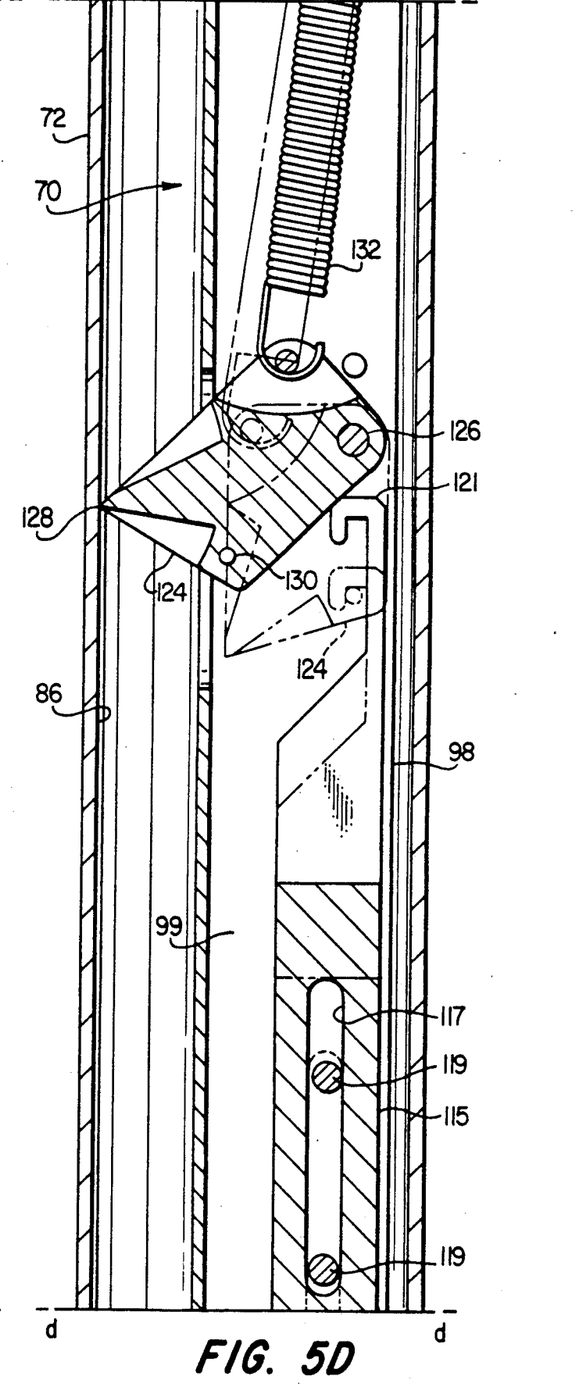
Figure 5E:
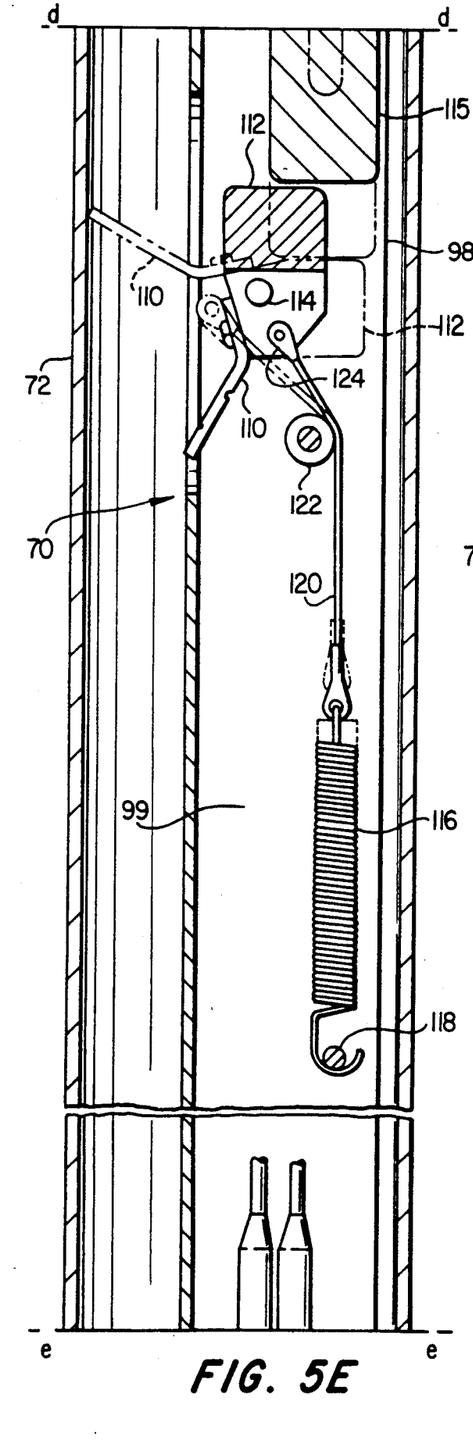
Figure 5F:
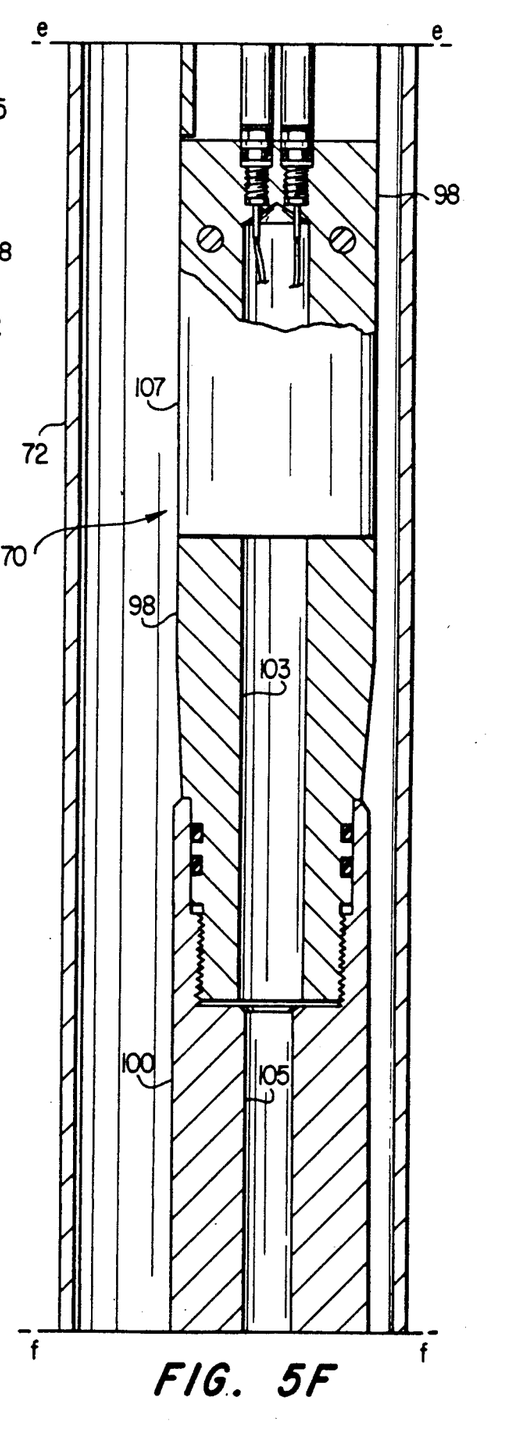
Figures 5G, 6, 7:
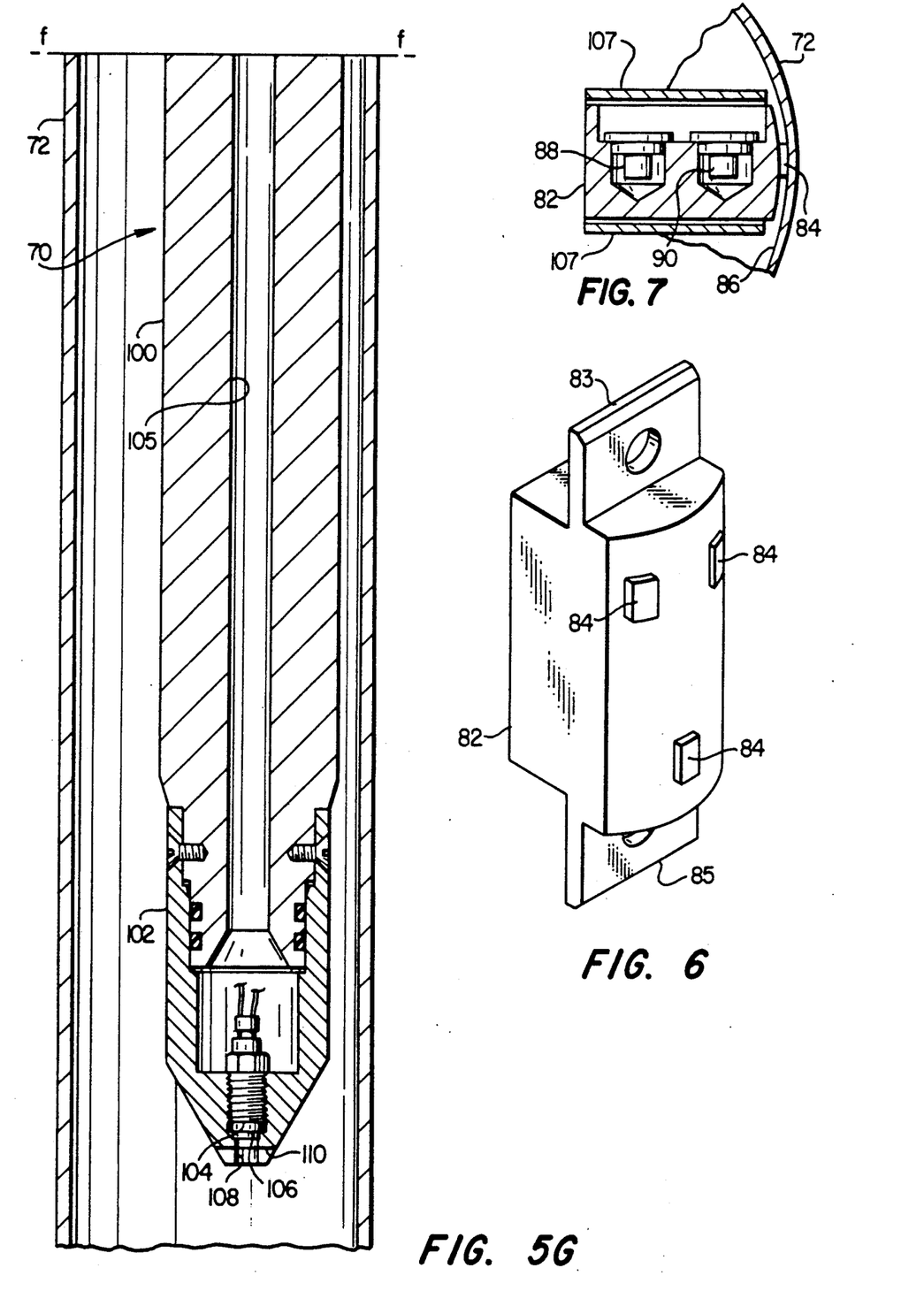
FIG. 6 is a perspective view of a portion of the apparatus shown in FIGS. 5A through 5G.
FIG. 7 is a section view taken along line 7—7 of FIG. 5B.

The lower section of the apparatus 70 illustrated in FIGS. 5C through 5G includes the body member 98 and an additional member 100 of a suitable length to add sufficient weight to the apparatus 70 to provide for traversal of the apparatus through a tubing string through which fluid may be flowing in opposition to the direction of movement of the apparatus. The lower end of the member 100, FIG. 5G, is connected to a cap 102 on which a pressure sensors suitably mounted. The pressure sensor 104 has a sensitive end face 106 mounted in a recess 108 from which one or more radial slots 110 extend to reduce the probability of containment of debris in the recess. Suitable passageways 103 and 105 are provided in the members 98 and 100, respectively, for training electrical conductors therethrough for the pressure sensor 104. The pressure sensor 104 may be used to generate signals for comparison with the signals generated by the accelerometers 88, 90 and 92 in accordance with the methods of the present invention.

Referring to FIGS. 5C thorough 5E, the body member 98 includes an elongated central slot 99 formed therein for accommodating a mechanism for locking the apparatus 70 in a selected position in the tubing 72 and with the body part 82 biased into engagement of its lugs 84 with the tubing wall 86. As shown in FIG. 5E, a trip finger 110 is supported for pivotal movement on the apparatus 70 and is connected to a cam 112 which is pivotally mounted on the member 98 and supported on a pivot pin 114. A coil spring 116 is anchored at one end by suitable anchor means 118 to the member 98 and is connected at its opposite end to a cable 120 which is trained over a sheave 122 and is connected at 124 to the cam 112.

The cam 112 is engageable with an elongated cam follower 115, see FIG. 5D also, supported on the member 98 for axial sliding movement in a direction generally parallel to the axis 73. The follower 115 includes an elongated slot 117 formed therein and which permits axial sliding movement of the follower between spaced apart stop pins 119. The follower 115 also includes a distal end portion 121 having a hook shape which is adapted to be connected to a locking finger 124 pivotally mounted on the apparatus 70 for movement about a pivot formed by a pin 126. The finger 124 includes a pointed end 128 engageable, in a released position, with the tubing inner wall 86 to bias the apparatus 70 into engagement with the tubing 72 in the position illustrated in FIGS. 5A through 5G and under the urging of the weight of the apparatus itself. A transversely extending pin 130 is supported on the finger 124 and is engageable with the hook 121 to hold the finger in a retracted position as shown by the dashed lines in FIG. 5D to permit insertion of the apparatus into a tubing string. A coil spring 132 is anchored at one end to the member 98 and at the opposite end to the finger 124 to urge the finger 124 into an extended position in engagement with the tubing wall 86, as shown.

Accordingly, the apparatus 70 may be lowered into a tubing string in a wellbore or the like with the finger 124 in the retracted position and the finger 110 extended and dragging along the tubing wall until a selected position of the apparatus is reached whereupon an upward pulling movement on the apparatus will cause the finger 110 to pivot in a counter-clockwise direction, viewing FIG. 5E to move the follower 115 upwardly releasing the finger 124 for pivotal movement to the position shown. Upon relaxing upward tension on the apparatus 70 as provided by a cable or tubing to which the apparatus is connected, the apparatus will be urged to move downwardly under its own weight and the finger 124 will bias the apparatus into a position into firm and forcible engagement of the lugs 84 with the tubing wall 86. In such a position the apparatus 70 will be adapted to sense lateral and torsional vibrations of the tubing string 72 by the accelerometers 88 and 90, axial vibrations by the accelerometer 92 and pressure fluctuations by the sensor.

As discussed in U.S. Pat. No. 4,715,451 and publications by the Society of Petroleum Engineers, P.O. Box 833836, Richardson, Tex. 75083 and identified as Papers Nos. 14327 and 15560 entitled "Detection of Various Drilling Phenomena Utilizing High Frequency Surface Measurements" and "A Study of Excitation Mechanisms and Resonances Inducing BHA Vibrations", respectively, the location of an event in the tubing 72, for example, may be determined by measuring torsional vibrations and axial vibrations which exhibit a particular relationship or coherency and with the known longitudinal and torsional wave speed in the material of which the tubing is made, the time difference between the arrival of a torsional signal as compared with an axial signal at the apparatus 70 can be used to determine the location of the event such as a crack or point of leakage in the tubing 72, the operation of a gas lift valve, or some other event which has a particular definable signature.

Although the methods and apparatus in accordance with the present invention have been described in some detail herein, those skilled in the art will recognize that various substitutions and modifications may be made without departing from the scope and spirit of the invention as recited in the appended claims.

What we claim is:

1. A method for determining the occurrence of an event in an elongated conduit comprising the steps of:
   providing first and second sensor means operably connected to said conduit for generating signals related to sensing at least one of axial or torsional vibrations of said conduit in response to said event;
   recording said signals as a function of time;
   determining the time difference between arrival of vibrations which generate signals at said first sensor means and said second sensor means, respectively, by
   (1) subjecting a plurality of multiple point consecutive time records for each signal to fast Fourier transform analysis of the time domain data to produce auto spectra values of said first sensor signal, $G_{aa}$, and said second sensor signal, $G_{rr}$, respectively;
   (2) calculating the cross spectra values, $G_{ar}$, of the respective series of time records of said first and second signals, respectively;

(3) summing the auto spectra values and the cross spectra values and determining averages of each, respectively;

(4) calculating the impulse response by determining the inverse Fourier transform of the ratio of the averaged cross spectra to the averaged auto spectra of at least one of said auto spectra;

(5) plotting the resultant values of said inverse Fourier transforms as a function of time to determine a peak value of such resultant values from time = O to determine said time difference; and (6) determining the location of said event based on said time difference and the acoustic velocity of a stress wave in said conduit.

2. The method set forth in claim 1 including the steps of:

prior to calculating said impulse response determining the frequency response of said conduit to said event by:

(a) impacting said conduit at a predetermined point with a signal, h, whose amplitude-time characteristic is measured;

(b) measuring the signals received, a and r, as a function of time at said first and second sensor means, respectively;

(c) performing fast Fourier transform analysis on a plurality of multiple point time records of signals a and r, respectively, of the time domain data of said signals to obtain the auto spectra, $G_{hh}$, and $G_{rr}$, and determining the cross spectra, $G_{ha}$ and $G_{hr}$ all as running averages;

(d) determining the frequency response of said conduit from the relationships;

$$R_a = \frac{G_{ha}}{G_{hh}}$$

and $$R_r = \frac{G_{hr}}{G_{hh}};$$

(e) deconvolving the frequency response of said conduit by performing the calculations of at least one of the relationships:

$$\frac{G_{ar}}{G_{aa}} \cdot \frac{R_a}{R_r} \text{ or }$$

$$\frac{G_{rr}}{G_{ar}} \cdot \frac{R_a}{R_r}, \text{ and}$$

then calculating the impulse response with the products of said at least one of said relationships.

3. The method set forth in claim 1 wherein:
said first sensor means senses torsional vibrations, said second sensor means senses axial vibrations and the location of said event from said first and second sensor means is determined from the equation $$m = \frac{V_r \cdot V_a \cdot \Delta t}{\Delta V}$$

wherein m is the distance of said event from said first and second sensor means,
$V_r$ is the torsional wave speed in said conduit,
$V_a$ is the axial wave speed in said conduit,
$\Delta V$ is $V_a - V_r$, and $\Delta t$ is the time difference of arrival of said torsional vibration and said axial vibration at said first and second sensor means.

4. A method for determining the occurrence of an event in an elongated conduit comprising the steps of:
providing first and second sensor means operably associated with said conduit for sensing vibrations of said conduit and pressure fluctuations of fluid in said conduit in response to said event;
comparing signals generated by said first and second sensor means to determine at least one of the location or nature of said event.

5. The method set forth in claim 4 wherein:
the location of said event from said first and second sensor means is determined from the equation $$m = \frac{V_f \cdot V_a \cdot \Delta t}{\Delta V}$$

wherein m is the distance of said event from said first and second sensor means,
$V_f$ is the acoustic velocity of fluid in said conduit,
$V_a$ is the axial wave speed of axial vibration in said conduit,
$\Delta V$ is $V_a - V_f$, and
$\Delta t$ is the time difference of arrival of said pressure fluctuation and said axial vibration at said first and second sensor means.

6. The method set forth in claim 4, wherein:
the location of said event from said first and second sensor means is determined from the equation $$m = \frac{V_f \cdot V_r \cdot \Delta t}{\Delta V}$$

wherein m is the distance of said event from said first and second sensor means,
$V_f$ is the acoustic velocity of fluid in said conduit,
$V_r$ is the torsional wave speed of torsional vibration in said conduit,
$\Delta V$ is $V_r - V_f$, and
$\Delta t$ is the time difference of arrival of said pressure fluctuation and said torsional vibration at said first and second sensor means.

7. The method set forth in claim 4 wherein:
said first sensor means is provided as a section of said conduit having accelerometer means mounted thereon for sensing vibrations transmitted in at least one of an axial or torsional direction with respect to said conduit.

8. The method set forth in claim 7 including the steps of:
recording said signals as a function of time;
comparing said signals by cross correlating said signals to determine the time difference between arrival of vibration which generate said signals at said first sensor means and said second sensor means, respectively, and determining the location of said event based on said time difference and the acoustic velocity of a stress wave in said conduit.

9. A method for determining the occurrence of an event in an elongated fluid conducting conduit comprising the steps of:
providing means disposed in said conduit at a predetermined position and including axial vibration sensing means, and torsional vibration sensing means for sensing axial and torsional vibrations of said conduit, respectively, and means for sensing changes in fluid pressure in said conduit; and comparing signals generated by said means for sensing changes in said pressure with signals generated by at least one of said means for sensing axial vibrations or torsional vibrations in said conduit for determining at least one of the location or nature of said event.

10. The method set forth in claim 9 including the steps of:

placing said means for sensing in said conduit at said predetermined location and securing said means for sensing in forcible contacts with said conduit.

11. The method set forth in claim 9 wherein;

the location of said event from said axial vibration sensing means and said torsional vibration sensing means is determined from the equation $$m = \frac{V_r \cdot V_a \cdot \Delta t}{\Delta V}$$

wherein m is the distance of said event from said axial vibration sensing means and said torsional vibration sensing means, $V_r$ is the torsional wave speed in said conduit, $V_a$ is the axial wave speed in said conduit, $\Delta V$ is $V_a - V_r$, and $\Delta t$ is the time difference of arrival of said torsional vibration and said axial vibration at said torsional vibration sensing means and said axial vibration sensing means, respectively.

12. A method for determining the occurrence of an event in an elongated fluid conducting conduit comprising the steps of:

providing means disposed in said conduit at a predetermined position and including axial vibration sensing means and torsional vibration sensing means for sensing axial and torsional vibrations of said conduit, respectively, and comparing first signals generated by said axial vibration sensing means and second signals generated by said torsional vibration sensing means, respectively, for determining the location of said event in said conduit by determining the time difference between arrival of vibrations which generate said first and second signals by:

(1) subjecting a plurality of multiple point consecutive time records for each signal to fast Fourier transform analysis of the time domain data to produce auto spectra values of said first signal, $G_{aa}$, and said second signal, $G_{rr}$, respectively;

(2) calculating the cross spectra values, $G_{ar}$, of the respective series of time records of said first and second signals, respectively;

(3) summing the auto spectra values and the cross spectra values and determining averages of each, respectively;

(4) calculating the impulse response by determining the inverse Fourier transform of the ratio of the averaged cross spectra to the averaged auto spectra of at least one of said auto spectra; and (5) plotting the resultant values of said inverse Fourier transforms as a function of time to determine a peak value of such resultant values from time = O to determine said time difference.

13. The method set forth in claim 12 including the steps of:

prior to calculating said impulse response determining the frequency response of said conduit to said event by:

(a) impacting said conduit at a predetermined point with a signal, h, whose amplitude-time characteristic is measured;

(b) measuring the signals received, a and r, as a function of time at said first and second sensor means, respectively;

(c) performing fast Fourier transform analysis on a plurality of multiple point time records of signals a and r, respectively, of the time domain data of said signals to obtain the auto spectra, $G_{hh}$, and $G_{rr}$, and determining the cross spectra, $G_{ha}$ and $G_{hr}$ all as running averages;

(d) determining the frequency response of said conduit from the relationships;

$$R_a = \frac{G_{ha}}{G_{hh}}$$

and $$R_r = \frac{G_{hr}}{G_{hh}};$$

(e) deconvolving the frequency response of said conduit by performing the calculations of at least one of the relationships:

$$\frac{G_{ar}}{G_{aa}} \cdot \frac{R_a}{R_r} \text{ or}$$

$$\frac{G_{rr}}{G_{ar}} \cdot \frac{R_a}{R_r}, \text{ and}$$

then calculating the impulse response with the products of said at least one of said relationships.

14. An apparatus insertable in an elongated tubular conduit for measuring vibratory movement of said conduit to determine at least one of the location of or nature of the occurrence of an event in said conduit, said apparatus comprising:

a first body part;

first accelerometer means mounted on said first body part for measuring vibrations in an axial direction with respect to said conduit;

second accelerometer means mounted on said first body part for measuring torsional vibrations in said conduit;

means movable at will for urging said first body part into forcible contact with said conduit; and means on said first body part for engaging a wall surface of said conduit for transmitting said vibrations from said conduit to said apparatus.

15. The apparatus set forth in claim 14 including:

pressure sensing means for measuring changes in pressure of fluid in said conduit.

16. An apparatus insertable in an elongated tubular conduit for measuring vibratory movement of said conduit to determine at least one of the location of or nature of the occurrence of an event in said conduit, said apparatus comprising:

a first body part;

first accelerometer means mounted on said first body part for measuring vibrations in an axial direction with respect to said conduit;

second accelerometer means mounted on said first body part for measuring torsional vibrations in said conduit;

means for urging said first body part into forcible contact with said conduit for transmitting said vibrations from said conduit to said apparatus; and means on said first body part for engaging a wall surface of said conduit at three spaced points on said conduit.

17. The apparatus set forth in claim 16 wherein:

said means for urging includes means responsive to changing the direction of movement of said apparatus upon insertion into said conduit.

18. An apparatus insertable in an elongated tubular conduit for measuring vibratory movement of said conduit to determine at least one of the location of or nature of the occurrence of an event in said conduit, said apparatus comprising:

a first body part;

first accelerometer means mounted on said first body part for measuring vibrations in an axial direction with respect to said conduit;

second accelerometer means, including at least two accelerometers, mounted on said first body party, said at least two accelerometers being disposed spaced apart from each other radially with respect to said axial direction of said conduit for measuring torsional vibrations in said conduit; and means for urging said first body part into forcible contact with said conduit for transmitting said vibrations from said conduit to said apparatus.

* * * * *